United States Patent [19]

Maggs

[11] Patent Number: 4,657,808

[45] Date of Patent: Apr. 14, 1987

[54] ACTIVATED CARBON PRODUCTS AND THEIR MANUFACTURE

[75] Inventor: Frederick A. P. Maggs, Salisbury, England

[73] Assignee: Charcoal Cloth Ltd., Maidenhead, England

[21] Appl. No.: 713,446

[22] Filed: Mar. 19, 1985

Related U.S. Application Data

[62] Division of Ser. No. 531,936, Sep. 13, 1983, Pat. No. 4,529,623.

[30] Foreign Application Priority Data

Sep. 13, 1982 [GB] United Kingdom ............... 8226038

[51] Int. Cl.$^4$ ............................................. B32B 7/00
[52] U.S. Cl. ..................... 428/263; 428/253; 428/254; 428/280; 428/281; 428/283; 428/289; 428/408; 428/913; 604/360
[58] Field of Search ................ 604/359, 360; 428/408, 428/280, 913, 281, 283, 289, 263, 253

[56] References Cited

U.S. PATENT DOCUMENTS

| | | | |
|---|---|---|---|
| 2,847,332 | 8/1958 | Ramadanoff | 428/408 |
| 3,847,833 | 11/1974 | Bailey et al. | 252/425 |
| 4,242,226 | 12/1980 | Siren | 252/422 |
| 4,274,979 | 6/1981 | Simpson | 252/422 |
| 4,409,125 | 10/1983 | Nishino et al. | 502/180 |

*Primary Examiner*—James J. Bell
*Attorney, Agent, or Firm*—Jeffers, Irish & Hoffman

[57] ABSTRACT

An activated carbon product such as a charcoal cloth or felt has, in addition to any activating material, a metal uniformly dispersed therein. The metal may be catalytic or bactericidal, and a particularly preferred product of the invention contains silver and is suitable for use as a surgical dressing. Such products can be produced by a conventional activation procedure using a mixture of halides, even if the further metal halide is substantially insoluble in the impregnation solution used for activation, by incorporating in the solution ammonia and a sequestering agent such as citric acid.

2 Claims, No Drawings

ACTIVATED CARBON PRODUCTS AND THEIR MANUFACTURE

This is a division of application Ser. No. 531,936, filed Sept. 13, 1983, now U.S. Pat. No. 4,529,623.

This invention relates to activated carbon products, in particular activated charcoal cloths and felts, and to methods for their manufacture. The products of this invention can be of, for example, bactericidal utility.

Various methods for producing activated charcoal cloths are known. For example, GB-A-1455531 discloses impregnating cellulose fibres with a reactive phosphorus compound and heating the impregnated fibres under certain conditions. The Kirk-Othmer Encyclopaedia of Chemical Technology, 16, 3rd Ed., 136 discloses the preparation of novoloid-based activated carbon in a one-step process, combining both carbonisation and activation, in an oxygen-free atmosphere containing steam and/or $CO_2$, at about 900° C. The products are said to have uniform pore size.

GB-A-1301101 discloses a particularly useful, and commercially used, process for preparing activated carbon products in fibrous form. Rayon, for example, is impregnated with a solution of inorganic halides, e.g. a mixture of ammonium, zinc and hexahydrated aluminium chlorides. The impregnation is followed by a controlled heating stage.

The utility of a carbonised fabric in surgical dressings has been appreciated for over 50 years. GB-A-386067 discloses surgical dressings comprising woven or entangled carbonised fibres. Such dressings are also disclosed as supports for therapeutic or antiseptic materials and it is stated that "the dressings will hold in considerable quantities iodine, formol, lime, oxygen, bacillary toxins, and the like". The use of, say, iodine in the dressings disclosed in GB-A-386067 appears to be a consequence of the adsorptive characteristics of charcoal cloths. Charcoal cloth is an excellent adsorbent for organic water-contaminants such as phenol, organic acids and insecticides. Charcoal cloth can also be used, e.g. in gas masks, to remove undesirable gases from the air.

EP-A-0053936 discloses surgical dressings comprising activated charcoal, preferably as activated charcoal cloth, impregnated with an anti-microbial agent, iodine being preferred. A characteristic of this disclosure is that no more than 20%, and preferably about 5%, of the adsorptive sites of the activated charcoal are saturated with the anti-microbial agent. Such a product probably contains less, say, iodine than an impregnated product as disclosed in GB-A-386067, but still suffers from the disadvantage that iodine is easily removed from the cloth in the presence of aqueous media. It is generally considered undesirable that free iodine should be allowed to come into contact with a wound, and yet this can be a problem associated with the use of surgical dressings, containing iodine, as disclosed in EP-A-0053936.

Charcoal cloth has considerable utility of its own as a wound dressing. It can adsorb unpleasant odours of the type which often emanate from infected wounds; in addition, it can adsorb bacteria.

Charcoal cloth may contain traces of elements used in the activation procedure. As can be seen, the nature of the product has made it easy to introduce other materials, such as bactericides, subsequently. Charcoal cloth post-impregnated with silver is also known, as a chemisorbent. It would nevertheless be desirable to extend the utility of charcoal cloth, e.g. in surgery, to take account of its inherent characteristics and to supplement them with properties which are not disadvantaged in the manner described above or in general as the result of mere surface application, by post-impregnation, of a desired additive.

According to the present invention, an activated charcoal product has, in addition to any activating material, a metal uniformly dispersed therein.

Metal elements of the compounds used to activate carbon in GB-A-1301101 are Zn, Al, Ca, Mg, Fe (which all have halides with the common, apparently essential, Lewis acid characteristics), Pb, Co and Ba. The metals used in the present invention are intended to provide the product with additional, beneficial properties, e.g. catalytic or bactericidal. Suitable metals for use in the invention are those of the Group VIII elements such as Fe or those of at. no. 76 to 78, e.g. Ir and Pt, and Group Ib, e.g. Ag or Cu.

It would obviously save time, labour and cost if, say, charcoal cloth could be impregnated with, say, the bactericidal metal silver, by use of a suitable silver compound at the same time as the activating compounds. For example, a procedural step is saved if the desired metal could be introduced with the halide solution used, before the heating steps, in the procedure of GB-A-1301101, rather than by impregnation after the activated material has been obtained.

However, if a solution of a soluble silver salt such as silver nitrate is added to a solution of halides as described in GB-A-1301101, insoluble silver halide is precipitated out. The result is poor, nonuniform impregnation of the charcoal cloth, or even no impregnation whatsoever, and the presence of potentially undesirable nitrate. A conventional attempt to overcome this problem, e.g. by the addition of ammonia which dissolves and prevents precipitation of silver chloride by forming complexed ions, causes precipitation of the activating elements zinc and aluminium, as their hydroxides, from the activating solution.

According to a second aspect of the present invention, a process for the preparation of an activated carbon product comprises treating a fibrous carbohydrate material with a solution of one or more Lewis acid halides of Zn, Al, Ca, Mg and Fe; a compound of a further metal element whose halide is relatively insoluble with respect to the, or the mixture of, Lewis acid halides; ammonia; and a sequestering agent; and then drying, carbonising and activating the carbohydrate material. The drying, carbonising and activating may be conducted in conventional manner, e.g. by the procedures described in GB-A-1301101, the contents of which are incorporated herein by reference.

The process of the invention allows the preparation of a product of the invention. The "further" metal element can be any of those described above as having desirable properties, supplementing those of the activated product, and which have substantially insoluble halides. Added metal element can be uniformly dispersed in the product to give the desired, e.g. catalytic or bactericidal activity. This can be achieved without the precipitation or other problems described above.

The sequestering agent is preferably a hydroxycarboxylic acid. A suitable hydroxycarboxylic acid is tartaric acid. Citric acid is presently most preferred.

The impregnating solution is suitably prepared by dissolving the Lewis acid or acids, e.g. a mixture of zinc and aluminium chlorides, in water, and then adding the sequestering agent, ammonia and a soluble salt of the desired metal. An ammoniacal silver halide solution could be used to supply both silver and ammonia.

The quantities of the materials contained in the solution can be determined fairly readily by simple experiment. However as a guide, if the solution contains, by weight, 3% ammonium chloride, 3% zinc chloride and 3% aluminium chloride hexahydrate, as mentioned above, it has been found that the addition of between 3% and 5% by weight citric acid prevents the formation of metal hydroxides when ammonium hydroxide is added to the solution, though greater amounts may be used if desired, particularly if the chloride concentrations are increased. The 3% values for chloride concentration are in fact optimum figures; as little as 2% could be used. 5% chloride might require about 7-8% citric acid.

Moreover, the amount of ammonium hydroxide required to suppress the formation of silver chloride (when the silver salt is added) is dependent on the amount of silver desired in the final impregnation solution, and can be determined by experiment. if cloudiness is observed in the solution, further ammonia can be added to remove precipitation.

While the preferred halides are the chlorides, fluorides, bromides and iodides can be used in some cases (though evolution of HF during carbonisation is obviously disadvantageous). AgI and AgBr have sufficient solubility in ammonia to give solutions of the required concentration for impregnation (e.g. less than 0.1% by weight Ag).

The above description can be generalised when it is desired to disperse a metal other than silver in the product. In determining the amount of the metal which is desired, in accordance with the preceding description, the yield of charcoal cloth given by any normal method of manufacture will be generally known or can be easily established. The, say, catalytic or bactericidal effect which is desired in the product can be achieved at low levels. Thus, for example, the product will usually comprise at least 0.05 % or 0.1, and often at least 0.2, but need not contain more than 5, 2 or even 1, and often no more than 0.5, by weight Ag or other desired metal. A product of the invention can be seen, by suitable microscopic examination, to have a uniform distribution of very small particles of, say, silver or silver oxide, extending through the thickness of the product. It can be seen quite clearly as distinct from a post-impregnated product, where relatively large agglomerations of the, say, silver of silver oxide are present, and at the surface of the product.

Other than the presence of the added material, a product of the invention can have all the characteristics associated with activated carbon products. It may be produced in the usual way, e.g. from rayon. It may be a felt or a knitted or, typically, woven cloth. A cloth, typically from 0.2 to 1 mm thick, containing uniformly distributed silver, can be advantageously used as a surgical dressing or chemisorbent.

The method and products of the inventions, and their utility, will now be illustrated.

EXAMPLE 1

To approximately 5 liters of tap water were added:
ammonium chloride: 225 g
zinc chloride: 225 g
aluminium chloride: 225 g
citric acid: 300 g
880 ammonia (fresh bottle): 900 cm$^3$ An aqueous solution containing 15 g silver nitrate in c. 400 cm$^3$ distilled water was made up and acidified with nitric acid (20%; 5 cm$^3$). (This addition is intended to prevent seed crystals of silver chloride forming). This solution was kept stoppered and in a dark place.

The silver nitrate solution was added to the bulk liquid (stirred) in aliquots of about 25–50 cm$^3$. White precipitation quickly disappeared. The addition of the final aliquot produced a persistent white precipitation and a further addition of 880 ammonia (200 cm$^3$) was made. The solution became clear again. Volume was adjusted to 7.5 dm$^3$ to give an impregnation solution containing:

| | |
|---|---|
| ammonium chloride | 3% |
| zinc chloride | 3% |
| aluminium chloride | 3% |
| citric acid | 4% |
| ammonia | ca 385 g (assuming 35% wt/vol) (i.e. 1100 cm$^3$) |
| silver nitrate | 0.2% |

Three lengths of rayon cloth (25 cm×5 m) were dipped separately into a shallow trough containing the impregnation solution. Dipping time was approximately 2 seconds; rolls following on and being allowed to drain with intermittent turning. The lengths were each rolled at 345 kPa and plant oven-dried (at 125° C.) by a single pass.

A silver analysis was made on a 3 g sample. The analysis was conducted by ashing a sample at 750° C., moistening the resultant ash with concentrated nitric acid, and re-igniting the moistened sample to constant weight, in order to ensure that all halides were expelled. The final residue was boiled with 10 cm$^3$ 8 M nitric acid and the entire solution diluted and titrated directly against standardised potassium thiocyanate solution using the Volhard procedure. The silver content was 0.23% by weight.

EXAMPLE 2

Four pieces of rayon felt (25×46 cm) were separately dipped into a shallow trough containing the impregnation solution used in Example 1. Dipping time was approximately 5 seconds. The pieces were rolled consecutively onto a 38 mm diameter tube and drained with intermittent turning. The pieces were ovendried without pressure by residence of some ten minutes.

All samples were stored in polypropylene sheet and again in black pvc to reduce ultraviolet penetration pending charring of the samples. All samples were charred at 360° C. in carbon dioxide, followed by activation in carbon dioxide at 950° C.

The silver content, by the analysis described in Example 1, was 0.40% by weight.

The cloth and felt products of Examples 1 and 2 have been demonstrated as active against *Staphylococcus aureus* (Oxford), *Bacillus subtilis* NCTC 8236, E. coli DCO and its envelope mutant DC2, and *Pseudomonas aeruginosa* 799 and its envelope mutant 799/61. These results have been obtained in broth and on agar at dilutions of up to 1:100 (at least for the cloth of Example 1).

Products such as in the examples can be used in catalysis, e.g. the breakdown of arsine and phosphine. The term "Activating" is often used to describe only the heat-treatment of carbon products. Herein, the term also describes those elements, solutions etc. conventionally used in activating carbon.

I claim:

1. A surgical dressing which consists essentially of an activated charcoal cloth or felt having uniformly dispersed therein at least one first activating metal element selected from Zn, Al, Ca, Mg and Fe, and Ag as a second metal element.

2. A surgical dressing according to claim 1 in which the amount of silver is from 0.1 to 1 percent by weight.

* * * * *